United States Patent [19]

Clerici

[11] Patent Number: 4,912,280
[45] Date of Patent: Mar. 27, 1990

[54] OLEFIN DIMERIZATION METHOD

[75] Inventor: Mario G. Clerici, San Donato Milanese, Italy

[73] Assignees: Enricerche S.p.A., Milan; Enichem Augusta S.p.A., Palermo, both of Italy

[21] Appl. No.: 96,362

[22] Filed: Sep. 11, 1987

[30] Foreign Application Priority Data

Sep. 24, 1986 [IT] Italy ................................ 21798 A/86

[51] Int. Cl.$^4$ ............................................. C07C 2/24
[52] U.S. Cl. .................................... 585/516; 585/510; 585/533
[58] Field of Search ........................ 585/510, 516, 533

[56] References Cited

U.S. PATENT DOCUMENTS 4,418,235 11/1983 Haag et al. .......................... 585/533
4,542,251 9/1985 Miller ................................... 585/533

Primary Examiner—Curtis R. Davis
Attorney, Agent, or Firm—Hedman, Gibson, Costigan & Hoare

[57] ABSTRACT

Olefins with between 4 and 24 and preferably between 10 and 20 carbon atoms are selectively dimerized by using zeolite catalysts in acid form which are partially exchanged with salts of metals having a valency of two or more.

12 Claims, No Drawings

OLEFIN DIMERIZATION METHOD

This invention to an olefin dimerization method. More particularly, the invention relates to a method for the dimerization of linear olefins with between 4 and 24 and preferably between 10 and 20 carbon atoms.

The patent and scientific literature describes various methods for the oligomerization of olefinic compounds. The catalysts used in the known art, which can be of vary varied types and be either homogeneous or heterogeneous, are mainly active with lower olefins.

Moreover, the obtained reaction products, including dimers, generally have a rather wide molecular weight distribution. If the requirement is to selectively obtain the dimer in an efficient manner, the known methods and catalysts demonstrate their limits, particularly if a long-chain olefin is to be dimerized. In this respect, known catalysts are sufficiently active only with the lower olefins.

Said known catalysts can be organometallic complexes, which are difficult to synthesize and are sensitive to atmospheric agents, or can be very strong acids such as $BF_3$, which have to be recovered on termination of the reaction and present the problems associated with homogeneous acid catalysis.

Among the known catalytic systems there are some of zeolite type, but the products obtained with these latter catalysts are a rather complex mixture deriving from both cracking and oligomerization reactions.

An example of this latter type of catalyst is described in European patent application 150105.

Zeolite catalysts of the known art are therefore particularly useful in converting lower olefins into a more easily usable product having a higher boiling point, but are unsuitable for the selective dimerization of olefins.

It has been surprisingly found possible, with high conversion and selectivity, to dimerize olefins with between 4 and 24 and preferably between 10 and 20 carbon atoms by using acid zeolite catalysts exchanged with suitable salts.

The present invention provides a method for the dimerization of olefins, in particular linear olefins, with between 4 and 24 and preferably between 10 and 20 carbon atoms, codmprising bringing a stream containing one or more olefins having a number of carbon atoms lying within said range into contact with a catalyst consisting of a zeolite in acid form, characterised in that the zeolite is partially in acid form and partially exchanged with cations of one or more bivalent or trivalent metals, the remainder being exchanged with alkaline metals, fhe dimerization reaction being conducted at a temperature not exceeding 280° C.

The catalysts used in the method according to the present invention are obtained from natural or synthetic zeolites in a form exchanged with alkaline metals, of the faujasite X and Y type, by firstly exchanging the natural or synthetic zeolite with an ammonium salt in order to replace at least 50% of the alkaline metal cations present on the zeolite with ammonium, then calcining at a temperature of between 400° and 600° C., preferably 500° C., to convert the zeolite into partially acid form, then subjecting it to partial ion exchange with the salt of a bivalent or trivalent metal, and finally drying at moderate temperature. The catalyst obtained by the aforesaid procedure is one which is exchanged to the extent of 10–50% with the originally present alkaline metal and to the extent of 1–30% with the bivalent or trivalent metal, the remainder being acid sites. The aforesaid preparation procedure relates to commercial starting materials, ie natural or synthetic zeolites exchanged with alkaline cations.

If a completely acid zeolite is to be used, this must be exchanged to the extent of 10–50% with an alkaline cation and to the extent of 1–30% with a bivalent or trivalent metal cation, the rest remaining acid.

The bivalent or trivalent metal cations derive from water-soluble salts of bivalent or trivalent metals, preferably Fe, Co, Ni, La, Ca, Ba, Sr, Cu, Nd or Zn, and preferably from sulphates, nitrates or acetates of the aforesaid metals, and more preferably from halides, particularly chlorides.

The catalyst pdrepared in this manner demonstrates strong activity in the dimerization of $C_4$–$C_{24}$ olefins with high selectivity and conversion. The reaction is preferably conducted in the liquid phase at a temperature of between 50° C. and 270° C., and preferably between 120° C. and 200° C., in the presence or absence of an inert solvent at atmospheric or greater than atmospheric pressure. The reaction can be conducted batchwise or continuously, the reaction products being separated from the effluent and the unconverted reagents being recycled. High conversions are generally obtained, with a dimer selectivity exceeding 90%. The remaining reaction product is the trimer containing negligible quantities of higher oligomers. Cracking reactions are negligible under the described conditions.

With the method according to the present invention it is therefore possible to obtain a reaction product which by virtue of the fact that its chemical and physical properties are better defined within a narrow range of values possesses superior attributes for particular applications.

In this respect, by choosing a suitable olefin or olefin cut, for example $C_{12}$–$C_{14}$ n-olefins, a product can be obtained which after hydrogenation is particularly suitable in the formulation of lubricants because of its viscosity characteristics and narrow boiling range.

Some examples are given hereinafter to better illustrate the invention, but without any intention to limit it to or by these examples.

EXAMPLES 1–9

50 g of zeolite Y in sodium form (Union Carbide SK40) are suspended in a solution of 25 g of ammonium chloride in 100 cc of water. The suspension is heated under reflux for 2.5 hours, cooled, filtered and washed a number of times with distilled water. After drying at 100° C. the solid is calcined at 500° C. for 6 hours.

4 g of zeolite prepared in this manner are suspended in a solution of $1.85 \times 10^{-3}$ moles of the chosen salt (see Table 1) in 25 cc of water, and the suspension is heated under reflux for 2 hours. After cooling, the solid is separated, washed a number of times with deionised water and the dried at 100° C.

The exchanged zeolites have the composition shown in Table 1.

TABLE 1

| EXAMPLE | SALT USED FOR EXCHANGE | $SiO_2$ (weight %) | $Al_2O_3$ (weight %) | $Na^+$ (weight %) | METAL (weight %) EXCHANGED | WEIGHT LOSS at 450° C. (weight %) |
|---|---|---|---|---|---|---|
| 1 | $Fe(CH_3COO)_3,4H_2O$ | 56.81 | 16.76 | 2.53 | 2.13 | 11.23 |
| 2 | $FeCl_3,6H_2O$ | 54.94 | 15.54 | 1.41 | 3.30 | 17.69 |
| 3 | $Cu(CH_3COO)_2,H_2O$ | 55.68 | 15.75 | 2.95 | 2.17 | 13.68 |
| 4 | $CuCl_2,2H_2O$ | 53.85 | 15.86 | 1.66 | 1.03 | 21.67 |
| 5 | $LaCl_3,nH_2O$ | 51.51 | 16.34 | 1.84 | 3.76 | 22.86 |
| 6 | $CaCl_2,6H_2O$ | 52.81 | 15.45 | 1.70 | 0.16 | 24.81 |
| 7 | $NiCl_2,6H_2O$ | 57.31 | 16.48 | 2.30 | 1.99 | 15.28 |
| 8 | $CoCl_2,H_2O$ | 52.28 | 15.31 | 1.64 | 0.977 | 25.76 |
| 9 | $Co(CH_3COO)_2,4H_2O$ | 52.81 | 15.51 | 2.66 | 2.21 | 22.43 |

EXAMPLES 10-18

0.5 g of zeolite Y exchanged as in Examples 1-9 are suspended in 10 cc of a $C_{14}H_{28}$ linear olefin mixture. After placing in a glass autoclave, the suspension is heated to 180° C. for 4 hours. After cooling, the suspension is filtered and the products analysed by gas chromatography and mass spectometry. The results are shown in Table 2.

TABLE 2

| EXAMPLE No. | CATALYST PREPARED AS IN EXAMPLE No. | CONVERSION (%) | SELECTIVITY TOWARDS | | |
|---|---|---|---|---|---|
| | | | DIMERS (%) | TRIMERS (%) | HIGHER OLIGOMERS (%) |
| 10 | 1 | 30 | 92 | 7 | 1 |
| 11 | 2 | 55 | 89 | 10 | 1 |
| 12 | 3 | 24 | 95 | 5 | — |
| 13 | 4 | 42 | 91 | 8 | 1 |
| 14 | 5 | 51 | 89.5 | 9 | 1.5 |
| 15 | 6 | 20 | 94 | 6 | — |
| 16 | 7 | 40 | 92 | 7 | 1 |
| 17 | 8 | 39 | 91.5 | 7 | 1.5 |
| 18 | 9 | 30 | 92 | 6.5 | 1.5 |

EXAMPLES 19-27

0.5 g of zeolite Y prepared as in Examples 1-9 are suspended in 10 cc of a $C_{12}$-$C_{14}$ linear olefin cut in a glass autoclave. After heating to 180° C. for 4 hours, the mixture is cooled, filtered and the liquid part analysed by gas chromatography and mass spectrometry. The results are shown in Table 3.

TABLE 3

| EXAMPLE No. | CATALYST PREPARED AS IN EXAMPLE No. | YIELD IN | | |
|---|---|---|---|---|
| | | $C_{24}$-$C_{28}$ (%) | $C_{36}$-$C_{42}$ (%) | HIGHER OLIGOMERS (%) |
| 19 | 1 | 27.5 | 2.1 | ≈0.2 |
| 20 | 2 | 50.1 | 5.3 | 0.5 |
| 21 | 3 | 23.1 | 1.2 | ≈0.1 |
| 22 | 4 | 38.9 | 3.7 | ≈0.2 |
| 23 | 5 | 46.1 | 4.9 | 0.4 |
| 24 | 6 | 18.1 | 1.5 | ≈0.1 |
| 25 | 7 | 37.9 | 2.9 | ≈0.3 |
| 26 | 8 | 38.3 | 3.2 | 0.4 |

TABLE 3-continued

| EXAMPLE No. | CATALYST PREPARED AS IN EXAMPLE No. | YIELD IN | | |
|---|---|---|---|---|
| | | $C_{24}$-$C_{28}$ (%) | $C_{36}$-$C_{42}$ (%) | HIGHER OLIGOMERS (%) |
| 27 | 9 | 29.2 | 2.6 | ≈0.2 |

I claim:

1. A process for the dimerization of olefins having 4 to 24 carbon atoms, comprising contacting a stream containing one or more of said olefins with a zeolite catalyst exchanged to the extent of about from 25% to about 50% with an alkali metal cation and to the extent of about from 1% to about 30% with cations of the bivalent or trivalent metal or metals, the remainder being at least substantially in acid form, wherein the zeolite catalyst is dried at moderate temperatures after incorporation of the bivalent or trivalent metal cations into the zeolite catalyst, and the dimerization reaction being conducted at a temperature not exceeding about 280° C.

2. The process as claimed in claim 1, wherein said bivalent or trivalent metal cations derive from bivalent or trivalent metals salts.

3. The process as claimed in claim 2, wherein said bivalent or trivalent metal salts are Fe, Co, Ni, La, Nd, Ca, Ba, Sr, Cu or Zn salts.

4. The process as claimed in claim 3, wherein said salts are chosen from nitrates, sulfates and acetates.

5. The process as claimed in claim 3, wherein said salts are halides.

6. The process as claimed in claim 5, wherein said halides are chlorides.

7. The process as claimed in claim 1, wherein the dimerization reaction is conducted at a temperature within from about 50° C. to about 270° C.

8. The process as claimed in claim 1, wherein the dimerization reaction is conducted with said olefins in liquid phase.

9. The process as claimed in claim 1, wherein the reaction is conducted in the presence of an inert solvent.

10. The process as claimed in claim 1, wherein said olefins are linear olefins.

11. The process as claimed in claim 1, wherein said olefins contain from about 10 to about 20 carbon atoms.

12. The process as claimed in claim 1, wherein the zeolite catalyst is exchanged to the extent of from about 35% to about 50% with an alkali metal cation.

* * * * *